(12) United States Patent
Tanaka et al.

(10) Patent No.: US 8,415,487 B2
(45) Date of Patent: Apr. 9, 2013

(54) PROCESS FOR PREPARING (3R)-2'-(4-BROMO-2-FLUOROBENZYL)SPIRO-[PYRROLIDINE-3,4'(1'H)-PYRROLO[1,2-A]PYRAZINE]-1',2,3',5(2H')-TETRAONE

(75) Inventors: Daisuke Tanaka, Osaka (JP); Toshiyuki Negoro, Sennan-gun (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 0 days.

(21) Appl. No.: 13/239,731

(22) Filed: Sep. 22, 2011

(65) Prior Publication Data

US 2012/0010405 A1   Jan. 12, 2012

Related U.S. Application Data

(62) Division of application No. 12/309,104, filed as application No. PCT/JP2007/061888 on Jun. 13, 2007, now Pat. No. 8,058,456.

(30) Foreign Application Priority Data

Jul. 7, 2006 (JP) ................................. 2006-187588

(51) Int. Cl.
*C07D 207/444*     (2006.01)
(52) U.S. Cl.
USPC ........................................................ 548/546
(58) Field of Classification Search ................... 548/546
See application file for complete search history.

(56) References Cited

U.S. PATENT DOCUMENTS 5,258,382 A   11/1993   Negoro et al.

FOREIGN PATENT DOCUMENTS

| JP | 4-164066 | 6/1992 |
| JP | 5-186472 | 7/1993 |
| JP | 6-192222 | 7/1994 |

OTHER PUBLICATIONS

International Search Report dated Jul. 31, 2007 in the International (PCT) Application PCT/JP2007/061888.
English translation of PCT Written Opinion dated Jan. 29, 2009 in the International (PCT) Application PCT/JP2007/061888 of which the parent application is the U.S. National Stage.
Toshiyuki Negoro et al., "Novel, Highly Potent Aldose Reductase Inhibitors: (R)-(—)-2-(4-Bromo-2-fluorobenzyl)-1,2,3,4-tetrahydropyrrolo[1,2-a]pyrazine-4-spiro-3'-pyrrolidine-1,2',3,5'-tetrone (AS-3201) and Its Congeners", Journal of Medicinal Chemistry, vol. 41, pp. 4118-4129, 1998.
Jordan, V.C. Nature Reviews: Drug Discovery, 2, 2003, 205.
Dörwald, F. Zaragoza, Side Reactions in Organic Synthesis: A Guide to Successful Synthesis Design, Weinheim: WILEY-VCH Verlag GmbH & Co. KGaA, 2005, Preface.

*Primary Examiner* — Douglas M Willis

(74) *Attorney, Agent, or Firm* — Wenderoth, Lind & Ponack, L.L.P.

(57) ABSTRACT

The present invention is a process for preparing (3R)-2'-(4-bromo-2-fluorobenzyl)spiro-[pyrrolidine-3,4'(1'H)-pyrrolo [1,2-a]pyrazine]-1',2,3',5(2H')-tetraone, comprising, for example, the following steps:
(1) reacting a compound of the formula (III)

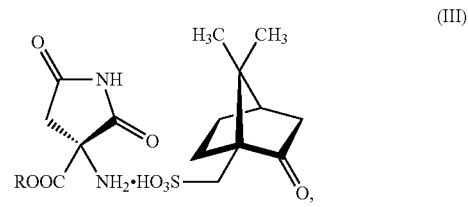

wherein R is a $C_{1-6}$ alkyl group,
with 2,5-dimethoxytetrahydrofuran to provide a compound of the formula (IV)

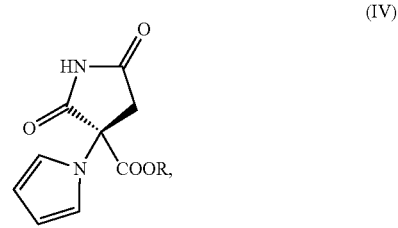

wherein R is a $C_{1-6}$ alkyl group;
(2) reacting the compound of the formula (IV)

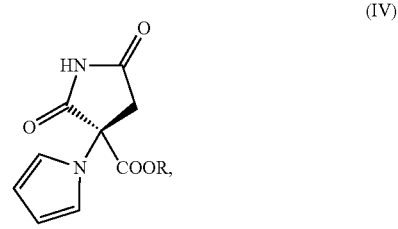

wherein R is a $C_{1-6}$ alkyl group,
with trichloroacetyl chloride to provide a compound of the formula

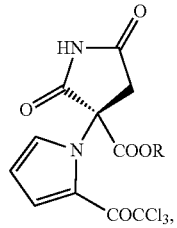

wherein R is a $C_{1-6}$ group; and
(3) reacting the compound provided in step (2) with 4-bromo-2-fluorobenzylamine to provide (3R)-2'-(4-bromo-2-fluorobenzyl)spiro-[pyrrolidine-3,4'(1'H)-pyrrolo[1,2-a]pyrazine]-1',2,3',5(2H')-tetraone.

8 Claims, No Drawings

PROCESS FOR PREPARING (3R)-2'-(4-BROMO-2-FLUOROBENZYL)SPIRO-[PYRROLIDINE-3,4'(1'H)-PYRROLO[1,2-A]PYRAZINE]-1',2,3',5(2H')-TETRAONE

CROSS-REFERENCE TO RELATED APPLICATIONS

This application is a divisional application of U.S. application Ser. No. 12/309,104, filed Jan. 7, 2009, now U.S. Pat. No. 8,058,456 now allowed, which is the national phase filing of International Patent Application No. PCT/JP2007/061888, filed Jun. 13, 2007.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

FIELD OF INVENTION

This invention relates to a novel 3-hydrazino-2,5-dioxopyrrolidine-3-carboxylate useful as an intermediate of active pharmaceutical ingredient of a therapeutic agent for diabetic complications, etc., and a process for preparing the same, as well as a process for preparing Ranirestat being useful as a therapeutic agent for diabetic complications using the intermediate.

DESCRIPTION OF RELATED ART

Tetrahydropyrrolo[1,2-a]pyrazin-4-spiro-3'-pyrrolidine derivatives which are promising therapeutic agents for diabetic complications showing a potent aldose reductase inhibitory activity are disclosed in the literature (for example, see JP-A-5-186472; and J. Med. Chem., 1998, 41, p. 4118 to 4129). Also Ranirestat [AS-3201; (3R)-2'-(4-bromo-2-fluorobenzyl)spiro[pyrrolidin-3,4'(1'H)-pyrrolo[1,2-a]pyrazine]-1',2,3',5(2H')-tetraone] selected among these derivatives has been developed clinically.

The process for preparing the compound of the formula (XI) mentioned below is described in a literature, and the literature describes that the optical resolution of the compound (wherein $R^4$ is a protecting group of a carboxyl group) into each enantiomer is carried out by forming diastereomer salts with an optically active acid [for example, (+)-camphor acid, (1S)-(+)- or (1R)-(−)-camphor-10-sulfonic acid, L-(+)- or D-(−)-tartaric acid, L-pyroglutamilic acid, (S)-(−)- or (R)-(+)-malic acid, hydrogenphosphate (S)-(+)- or (R)-(−)-1,1'-binaphthyl-2,2'-diyl, (−) or (+)-2'-nitrotartronic acid, D-(+)-tartronic acid, (−)-dibenzoyl-L-tartaric acid, (+)-dibenzoyl-D-tartaric acid, (−)-diacetyl-L-tartaric acid, etc.] according to the conventional method, followed by isolating the two diastereomer salts and converting them into free bases thereof (see, for example, JP-A-5-186472).

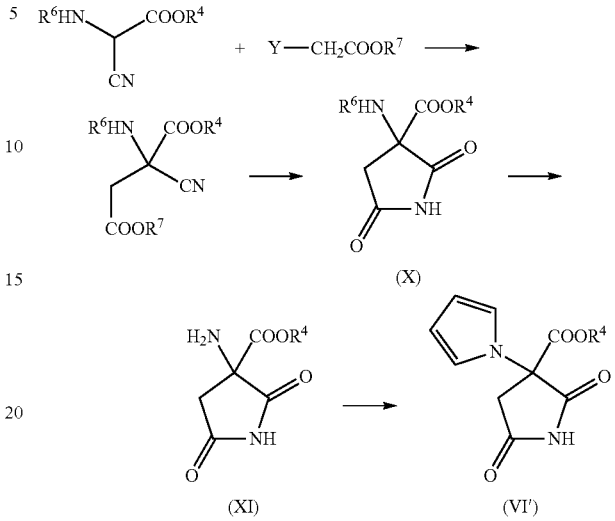

However there is no specific disclosure of the diastereomer salt of the compound of the formula (XI) (wherein $R^4$ is a protecting group of a carboxyl group) and no suggestion of a direct preparation of the compound of the formula (VI') mentioned above using the diastereomer salt.

A literature describes that racemic compounds (Ia) and (Ib) shown below can be resolved into two enantiomers by forming diastereomer salts with an optically active amine according to the conventional method, followed by separating them into two kinds of diastereomer salts by a fractional crystallization and then decomposing these salts (see, for example, JP-A-6-192222).

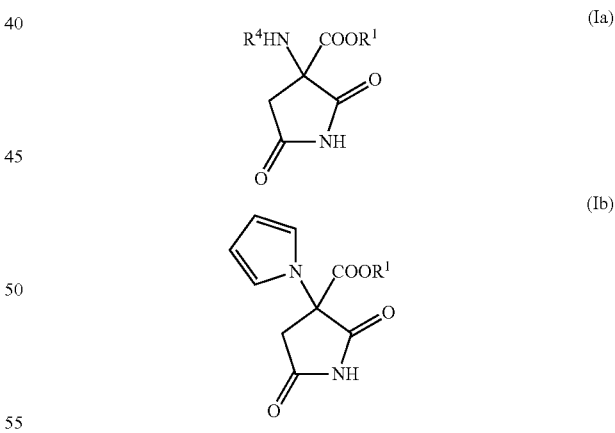

wherein $R^1$ is a protecting group of a carboxyl group and $R^4$ is a group cleavable by hydrogenolysis or a tert-butoxycarbonyl group, with proviso that when $R^4$ is a group cleavable by hydrogenolysis, then $R^1$ is a group cleavable by hydrolysis.

However there is no description and no suggestion on an optical resolution of the compound of the formula (Ia) wherein $R^4$ is a hydrogen atom.

The process for preparing Ranirestat is described in the literature as shown in the below scheme (see, for example, J. Med. Chem., 1998, 41, p. 4118 to 4129).

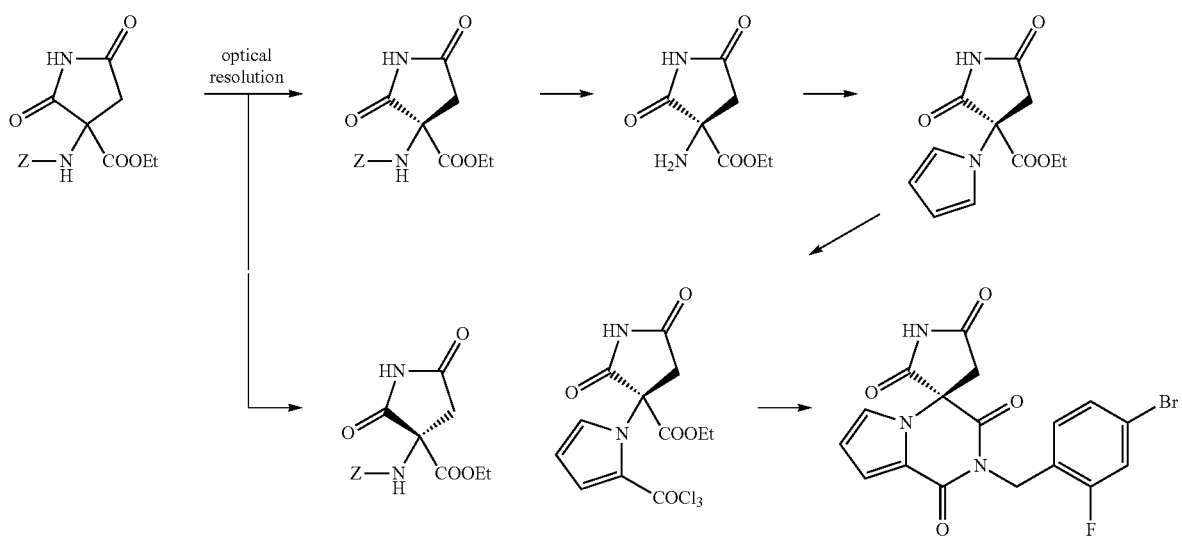

wherein Z is a benzyloxycarbonyl group.

However there is no description and suggestion on an optical resolution of racemic ethyl 3-amino-2,5-dioxopyrrolidine-3-carboxylate.

The process for preparing optically active 2,5-dioxo-3-(pyrrol-1-yl)pyrrolidine-3-carboxylates described in the literature requires essentially a step of removing an optically active amine used as an optical resolution agent by using an acid after an optical resolution of racemic intermediates and also requires a large number of steps as shown in the scheme below (see, for example, JP-A-6-192222 and J. Med. Chem., 1998, 41, p. 4118 to 4129).

DISCLOSURE OF INVENTION

Brief Summary of the Invention

Problems to be Solved by Invention

An object of the present invention is to provide a process for preparing active pharmaceutical ingredient of Ranirestat being a promising therapeutic agent for diabetic complications efficiently. Specifically, an object of the present invention is to provide a process for preparing optically active

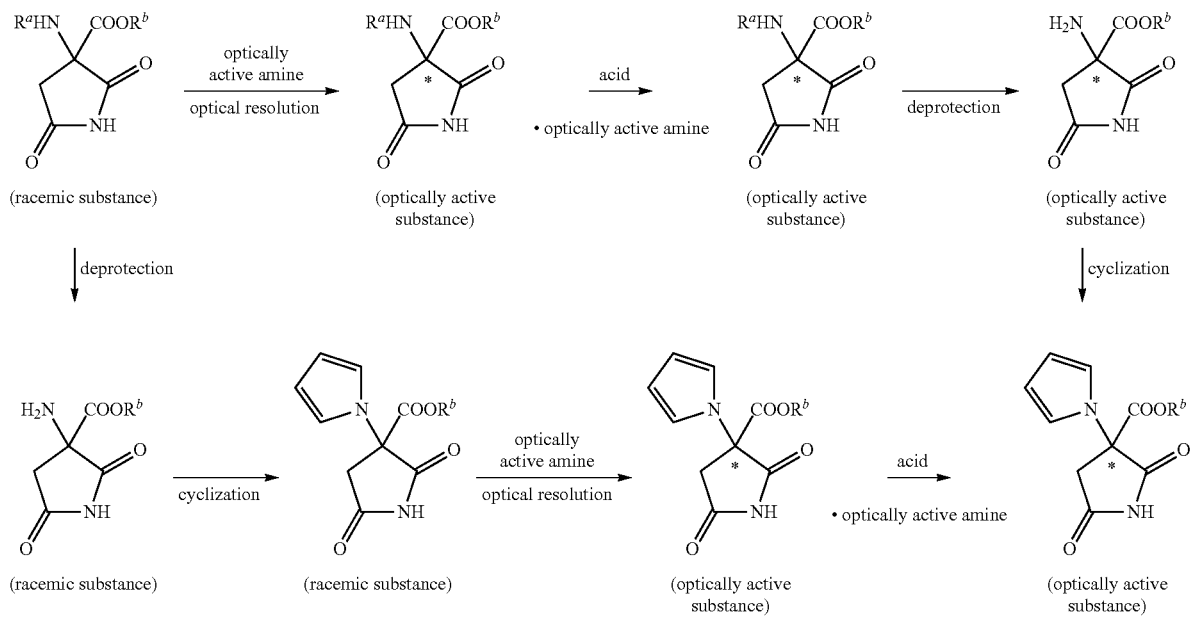

wherein $R^a$ is a protecting group for an amino group such as a benzylcarbonyl group and $R^b$ is a protecting group for a carboxyl group such as an ethyl group.

2,5-dioxo-3-(pyrrol-1-yl)pyrrolidine-3-carboxylates being one of key intermediates of Ranirestat more efficiently than those of the conventional method.

Means for Solving Problem

The present inventors have intensively studied in order to achieve the above-mentioned object, and have found that (1) most preferred optical resolution agent for 3-amino-2,5-dioxopyrrolidine-3-carboxylates (II) is (S)-(+)-camphorsulfonic acid, (2) a preparation of the (S)-(+)-camphorsulfonic acid salt (III) of the (R)-3-amino-2,5-dioxopyrrolidine-3-carboxylates by performing a step of preparing the 3-amino-2, 5-dioxopyrrolidine-3-carboxylates (II) and a step of optical resolution with the (S)-(+)-camphorsulfonic acid continuously to produce (S)-(+)-camphorsulfonic acid salt (III) of (R)-3-amino-2,5-dioxopyrrolidine-3-carboxylates; and (3) a step of preparing the ethyl (R)-2,5-dioxo-3-(pyrrol-1-yl)pyrrolidine-3-carboxylates (IV) directly from the (S)-(+)-camphorsulfonic acid salt (III) of (R)-3-amino-2,5-dioxopyrrolidine-3-carboxylates obtained via the optical resolution, and have accomplished the present invention.

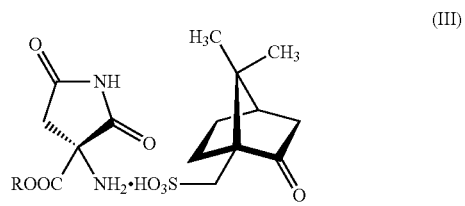

wherein R is as defined above,
with 2,5-dimethoxytetrahydrofuran.

[2] The process as set forth in [1], wherein R in the compound of the formula (III) is an ethyl group.

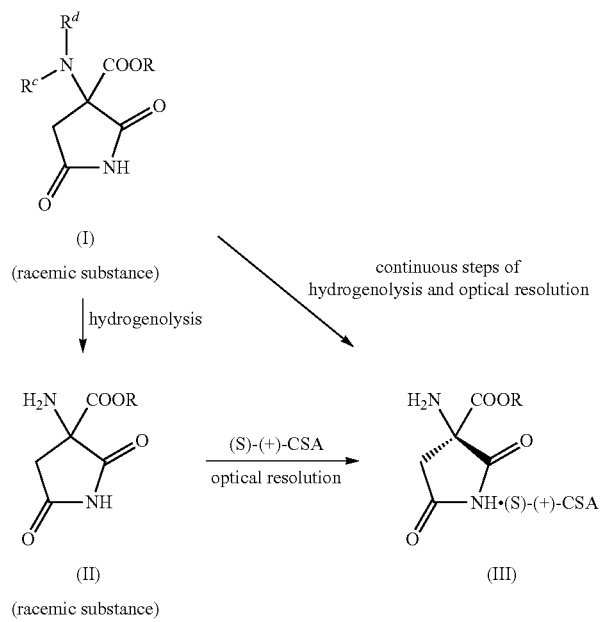

wherein R is a $C_{1-6}$ alkyl group; $R^c$ is a hydrogen atom or an optionally substituted benzyloxycarbonyl group; with the proviso that when $R^c$ is a hydrogen atom, then $R^d$ is an optionally substituted benzyloxycarbonyl group or an amino group; when $R^c$ is an optionally substituted benzyloxycarbonyl group, then $R^d$ is an optionally substituted benzyloxycarbonylamino group; and CSA is camphorsulfonic acid.

That is, the present invention relates to the following embodiments:

[1] The process for preparing a compound of the formula (IV):

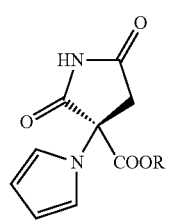

wherein R is a $C_{1-6}$ alkyl group,
comprising reacting a compound of the formula (III):

[3] The process as set forth in [1] or [2], wherein the reaction is carried out by adding a base to the solution of the compound of the formula (III) and 2,5-dimethoxytetrahydrofuran in acetic acid.

[4] The process as set forth in [3], wherein the base is sodium acetate.

[5] A process for preparing (3R)-2'-(4-bromo-2-fluorobenzyl)spiro-[pyrrolidine-3,4'(1'H)-pyrrolo[1,2-a]pyrazine]-1', 2,3',5(2H')-tetraone, comprising the step of preparing the compound of the formula (IV) as set forth in any one of [1] to [4]; and a step of converting the compound of the formula (IV) prepared in the preceding step into (3R)-2'-(4-bromo-2-fluorobenzyl)-spiro-[pyrrolidine-3,4'(1'H)-pyrrolo[1,2-a] pyrazine]-1',2,3',5(2H')-tetraone.

[6] A process for preparing (3R)-2'-(4-bromo-2-fluorobenzyl)spiro-[pyrrolidine-3,4'(1'H)-pyrrolo[1,2-a]pyrazine]-1', 2,3',5(2H')-tetraone, comprising the following steps:
(1) a step of preparing the compound of the formula (IV) as set forth in any one of [1] to [4];
(2) a step of converting 1-pyrrolyl group in the compound of the formula (IV) into 2-trichloroacetylpyrrol-1-yl group; and (3) a step of reacting the product of the above step (2) with 4-bromo-2-fluorobenzylamine to convert it into (3R)-2'-(4-bromo-2-fluorobenzyl)spiro[pyrrolidine-3,4'(1'H)-pyrrolo[1,2-a]pyrazine]-1',2,3',5(2H')-tetraone.

[7] A compound of the formula (III):

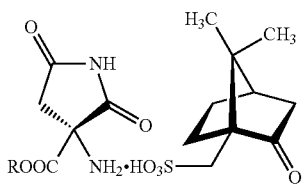

(III)

wherein R is a $C_{1-6}$ alkyl group.

[8] The compound as set forth in [7], wherein R is an ethyl group.

[9] A process for preparing the compound as set forth in [7], comprising a step of crystallizing the compound as set forth in [7] from a mixture of the compound of the formula (II):

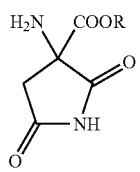

(II)

wherein R is a $C_{1-6}$ alkyl group, and (S)-(+)-camphorsulfonic acid dissolved in alcohols; and a step of isolating the crystal.

[10] A process for preparing the compound as set forth in [7], comprising a step of undergoing hydrogenolysis of the compound of the formula (I):

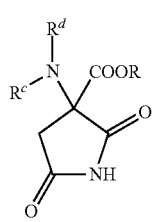

(I)

wherein R is a $C_{1-6}$ alkyl group; $R^c$ is a hydrogen atom or an optionally substituted benzyloxycarbonyl group; and when $R^c$ is a hydrogen atom, then $R^d$ is an optionally substituted benzyloxycarbonyl group or an amino group; when $R^c$ is an optionally substituted benzyloxycarbonyl group, then $R^d$ is an optionally substituted benzyloxycarbonylamino group, to prepare the compound of the formula (II):

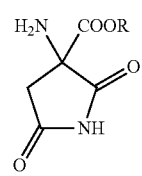

(II)

wherein R is as defined above;

a step of, without isolating the compound of the formula (II) prepared in the preceding step, forming a salt of the compound of the formula (II) with (S)-(+)-camphorsulfonic acid, followed by performing an optical resolution of it to prepare a crystal of the compound as set forth in [7]; and a step of isolating the crystal.

[11] A use of the compound as set forth in [7] or [8] in the manufacture of (3R)-2'-(4-bromo-2-fluorobenzyl)spiro-[pyrrolidine-3,4'(1'H)-pyrrolo[1,2-a]pyrazine]-1',2,3',5(2H')-tetraone.

[12] A process for preparing (3R)-2'-(4-bromo-2-fluorobenzyl)spiro-[pyrrolidine-3,4'(1'H)-pyrrolo[1,2-a]pyrazine]-1',2,3',5(2H')-tetraone, comprising using the compound as set forth in [7] or [8] as an intermediate or a starting material.

[13] The process as set forth in [12], characterized by preparing the compound as set forth in [7] or [8] by the process as set forth in any one of [1] to [4].

Effect of the Invention

The compound of the formula (III) is a novel salt of 3-amino-2,5-dioxopyrrolidine-3-carboxylates with an optically active acid obtained in high yields and with high purity. This salt can be used to prepare Ranirestat efficiently in shorter process compared to the conventional method. That is, the merit of the process of the present invention over those of the conventional process is as follows. The optical resolution of the compound of the formula (II) with (S)-(+)-camphorsulfonic acid is the most efficient process among the optical resolution process using an optically active acid and also is equal to the well-known optical resolution of other intermediates (for example, the optical resolution with optically active amine described in the aforementioned JP-A-6-192222 and J. Med. Chem., 1998, 41 p. 4118 to 4129) in terms of resolution yield and optical yield. In addition, the diastereomer salt obtained in the optical resolution can be prepared from the compound before two steps by continuous process. Also the aforementioned well-known process requires essentially a step of removing the optical resolution agent (an optically active amine) from the diastereomer salts and then isolating the free intermediate, while the process of the invention does not require the isolating step and thus the diastereomer salt obtained by the optical resolution can be converted directly into the intermediate of the next step in high yields. Further, it is difficult to recover the free optically active substance from the diastereomer salt obtained after the optical resolution, since the water-solubility of the compound of the formula (II) is high. Therefore the accomplishment of avoiding this recovery process by the present invention contributes largely to an efficient preparation of Ranirestat.

BRIEF DESCRIPTION OF THE SEVERAL VIEWS OF THE DRAWING(S)

Not Applicable

DETAILED DESCRIPTION OF THE INVENTION

Best Modes for Carrying Out the Invention

The present invention is explained in more detail below.

The compound of the formula (III) may exist in a hydrate and/or a solvate form, thus these hydrates and/or solvates are also included in the compound of the invention.

The terms used herein are explained as follows. Unless defined otherwise, the definition for each group shall also be applied to where said group is a part of another group.

The "$C_{1-6}$ alkyl group" is a straight chain or branched chain alkyl group having 1 to 6 carbon atoms, specifically such as methyl group, ethyl group, propyl group, isopropyl group, butyl group, isobutyl group, tert-butyl group, pentyl group, isopentyl group, neopentyl group and hexyl group, etc.

The (S)-(+)-camphorsulfonic acid may be indicated by (1S)-(+)-10-camphorsulfonic acid or (S)-(+)-camphor-10-sulfonic acid, and is represented by the following chemical structure:

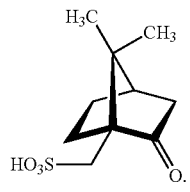

The "optionally substituted benzyloxycarbonyl group" is a benzyl group in which the benzene ring moiety may be optionally substituted by a halogen atom, a $C_{1-4}$ alkyl group, a $C_{1-4}$ alkoxy group, a cyano group or a nitro group. Specific examples include benzyl group, 4-chlorobenzyl group, 3-bromobenzyl group, 4-methylbenzyl group, 3-methylbenzyl group, 2-methoxybenzyl group, 4-methoxybenzyl group, 4-cyanobenzyl group, 4-nitrobenzyl group and benzyloxycarbonylamino group, etc.

The "optionally substituted benzyloxycarbonylamino group" is an amino group substituted by the above-mentioned optionally substituted benzyloxycarbonyl group.

Then the process for preparation of the present invention is explained in detail below.

The mixture of the compound of the formula (II) and (S)-(+)-camphorsulfonic acid can be crystallized from alcohols (for example, methanol, ethanol, isopropanol, etc.) and then the crystal precipitated is collected by filtering to give the diastereomer salt of the formula (III) selectively. This fractional crystallization can be carried out preferably using ethanol according to a conventional method. Usually, the mixture of the compound of the formula (II) and (S)-(+)-camphorsulfonic acid is dissolved in alcohols while heating and the resulting solution is concentrated as appropriate, and then cooled to crystallize the compound of the formula (III). The temperature for heating is not limited otherwise, but the reaction is usually heated until the alcohols are refluxed. Also when cooling, the crystal of the compound of the formula (III) may be added as the seed. The amount used of (S)-(+)-camphorsulfonic acid is preferably one equivalent to the compound of the formula (II) (the amount is not limited strictly to one equivalent). The amount of alcohols used in the fractional crystallization of 1 g of the compound of the formula (II) is usually 3 to 50 ml. But when a large amount of alcohols is used in this optical resolution, the compound of the formula (II) and (S)-(+)-camphorsulfonic acid are dissolved in the alcohols, then the resulting solution is preferably concentrated to 4 to 6 ml per 1 g of the compound of the formula (II). The rate for cooling is not limited otherwise, but is usually 0.25 to 2.5° C./min. Usually cooling is carried out at a room temperature to around 0° C. When crystallization is trouble, acetones such as acetone can be used effectively in place of alcohols. The crystal obtained by fractional crystallization can be recrystallized from alcohols according to a conventional method as appropriate to give the crystal with higher optical purity.

The compound of the formula (II) can be prepared by the well-known methods described in JP-A-5-186472 and JP-A-6-192222 as aforementioned or the novel processes described in Reference Examples 1 to 4 as mentioned below. The (S)-(+)-camphorsulfonic acid used as an optical resolution agent is commercially available.

The compound of the formula (I) wherein $R^c$ is an optionally substituted benzyloxycarbonyl group and $R^d$ is an optionally substituted benzyloxycarbonylamino group [the compound of the formula (I-1) below] can be prepared by a novel process illustrated in the following scheme.

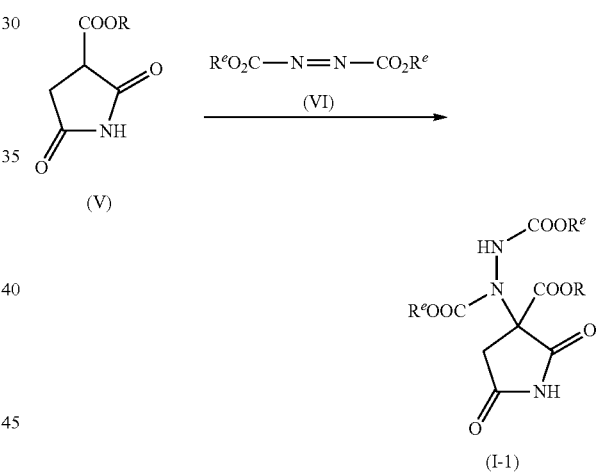

wherein R is a $C_{1-6}$ alkyl group and $R^e$ is an optionally substituted benzyl group.

Specific examples of the solvent used in the reaction of the compound of the formula (V) with the compound of the formula (VI) include methanol, ethanol, isopropanol, tert-butanol, ethyl acetate, acetonitrile, tetrahydrofuran, N,N-dimethylformamide, dimethylsulfoxide and water, etc., which can be used alone respectively or in a combination of two or more kinds thereof. The base is not necessarily required in this step, but a use of the base can proceed with the reaction more efficiently. Specific examples of the base include potassium carbonate, sodium carbonate, sodium bicarbonate, triethylamine, pyridine, 1,8-diazabicyclo[5.4.0]undeca-7-ene, sodium ethoxide and potassium tert-butoxide, etc. The amount used of the base is not limited otherwise, but can be selected from those ranging from a catalytic amount to an excess amount to those of the compound of the formula (V). The reaction temperature is usually at 0 to 100° C., preferably 10 to 30° C.

The compound of the formula (V) can be prepared by reacting a diethyl malonate with 2-chloroacetamide in the presence of the base in one step according to a method described in JP-A-60-16989 or a similar method thereto.

The compound of the formula (VI) is either commercially available, or can be prepared by the method that is well-known (or disclosed) in literatures or a similar method thereto.

The compound of the formula (I) wherein $R^c$ is a hydrogen atom and $R^d$ is an amino group [the compound of the formula (I-3) below] can be prepared by a process illustrated in the following scheme.

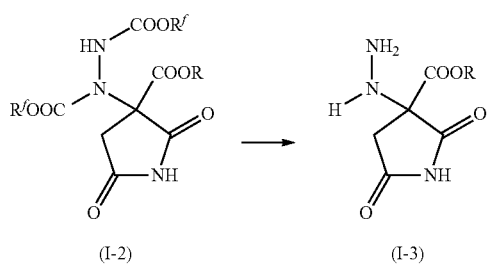

wherein R is a $C_{1-6}$ alkyl group and W is an optionally substituted benzyl group or a tert-butyloxycarbonyl group.

The compound of the formula (I-2) wherein $R^f$ is a tert-butyloxycarbonyl group is reacted with an acid in an appropriate solvent to produce the compound of the formula (I-3). Specific examples of the solvent used in the reaction include ethyl acetate, dichloromethane, 1,4-dioxane, acetic acid and water, etc., which can be used alone respectively or in a combination of two or more kinds thereof. Specific examples of the acid used in the reaction include hydrogen chloride, hydrogen bromide, hydrogen iodide, sulfuric acid, trifluoroacetic acid, methanesulfonic acid and trifluoromethanesulfonic acid, etc., with among them hydrogen chloride or trifluoroacetic acid being preferred. A preferred reaction temperature is at 0 to 30° C.

The compound of the formula (I-2) wherein $R^f$ is an optionally substituted benzyl group undergoes a hydrogenolysis in an appropriate solvent in the presence of catalyst such as palladium carbon ethylenediamine complex in a short duration to produce the compound of the formula (I-3). Specific examples of the solvent include ethyl acetate, methanol, ethanol, isopropanol and tetrahydrofuran, etc., which can be used alone respectively or in a combination of two or more kinds thereof. A preferred solvent is ethanol. The reaction temperature is usually at 0 to 80° C. The preferable reaction time is usually 1 to 4 hours at room temperature, but which depends on a kind of catalyst, a reaction temperature or a manner for stirring, etc.

The compound of the formula (I-2) can be prepared in a similar manner to those of the compound of the formula (I-1) as aforementioned.

The compounds of the formula (I-1) as well as the formula (I-3) (these compounds may form the salts thereof) is decomposed in a catalytic hydrogenolysis or a catalytic hydrogen transfer to produce the compound of the formula (II). The catalytic hydrogenolysis is carried out in an appropriate solvent under hydrogen at atmospheric pressure or increased pressure in the presence of a catalyst such as palladium-carbon, platinum-carbon, platinum oxide and Raney nickel, etc. Specific examples of the solvent include methanol, ethanol, isopropanol, acetic acid and water, etc., which can be used alone respectively or a combination of two or more kinds thereof. When a neutral solvent is used in the catalytic hydrogenolysis, an acid such as hydrogen chloride or trifluoroacetic acid, etc., may be added. The reaction temperature is usually at 0 to 80° C. The decomposition by catalytic hydrogen transfer can be carried out according to the method described in J. Heterocyclic Chem. 18, 31 (1981) and Indian J. Chem. 42B, 1774 (2003) or a similar method thereto. The source of hydrogen used includes, for example, ammonium formate, formic acid, cyclohexene and hydrazine, etc. Specific examples of the solvent include methanol, ethanol, isopropanol, acetic acid and water, etc., which can be used alone respectively or in a combination of two or more kinds thereof.

As shown in the Example 3 mentioned below, it can be carried out continuously the step of undergoing hydrogenolysis of the compound of the formula (I-1) to prepare the compound of the formula (II) and the step of performing the optical resolution of the compound of the formula (II) to prepare the compound of the formula (III).

The compound of the formula (I) wherein $R^c$ is a hydrogen atom and $R^d$ is an optionally substituted benzyloxycarbonyl group can be prepared by the process described in JP-A-5-186472 and JP-A-6-192222.

The compound of the formula (III) is reacted with 2,5-dimethoxytetrahydrofuran in an appropriate solvent to produce the compound of the formula (IV). The solvent is preferably a mixed solvent of water and organic solvent, and specific examples of the organic solvent include ethyl acetate, methanol and acetic acid, etc. The mixed ratio of the solvents can be varied depending on a type of the compound of the formula (III) used, with the mixed solvent wherein the ratio of organic solvent to water is 1 to 90% being preferred. The highly preferred mixed solvent is a mixed solvent of water and acetic acid (aqueous acetic acid solution), with 1 to 50% aqueous acetic acid being more preferred. The amount used of the mixed solvent is usually 3 to 20 ml per 1 g of the compound of the formula (III). When an aqueous acetic acid is used, a base (for example, sodium bicarbonate, sodium acetate, etc.) is preferably added. The amount of the base is preferably about 1 to 1.2 equivalents to the compound of the formula (III). The reaction temperature is usually at room temperature to 100° C.

The aforementioned JP-A-5-186472, JP-A-6-192222 and J. Med. Chem., 1998, 41, p. 4118 to 4129 describe that the compound of the formula (IV) is applicable as an intermediate or a starting material of Ranirestat being a promising therapeutic agent for diabetic complications described therein. Also as shown in Examples 4 to 7 mentioned below, the compound of the formula (III) of the present invention can be derivatized to Ranirestat by way of the compound of the formula (IV). Also JP-A-08-176105 describes that 2-ethoxycarbonyl-2-(2-trichloroacetylpyrrol-1-yl)succinimide, which can be prepared from the compound of the formula (IV) as a starting material, is an intermediate of 2-carboxysuccinimide derivatives useful as a therapeutic agent for diabetic complications. The compound of the formula (III) of the present invention having a chemically modifiable side chain can become an intermediate or a starting material useful in creating novel pharmaceuticals, since the 2,5-dioxopyrrolidine skeleton is a chemical structure often found in the substructure of compounds useful as pharmaceuticals such as a therapeutic agent for diabetes-related conditions or a central nervous system agents.

EXAMPLES

The present invention is illustrated in more detail below by Examples, but the present invention should not be construed

Example 1

Preparation of (S)-(+)-camphorsulfonic acid salt of ethyl (R)-3-amino-2,5-dioxopyrrolidine-3-carboxylate Ethyl 3-amino-2,5-dioxopyrrolidine-3-carboxylate (8.00 g) and (S)-(+)-camphorsulfonic acid (10.0 g) were dissolved in ethanol (80 ml) while warming and then this resulting solution was concentrated under reduced pressure to about 45 ml in total. This mixture was allowed to stand in ice-cooling and the crystal precipitated was corrected by filtering and then washed with ethanol. This crystal was recrystallized from ethanol to give the desired product (4.70 g) as crystal.

Melting point: 229-230° C. (decomposition). $[\alpha]_D^{27}$+10.2° (c 1.03, MeOH).

$^1$H NMR (400 MHz, D$_2$O, 23° C.) δ: 4.43 (2H, q, J=7.2 Hz), 3.56 (1H, d, J=18.8 Hz), 3.28 (1H, d, J=15.2 Hz), 3.22 (1H, d, J=18.8 Hz), 2.86 (1H, d, J=14.8 Hz), 2.46-2.37 (1H, m), 2.16 (1H, t, J=4.8 Hz), 2.09-2.00 (1H, m), 1.84 (1H, d, J=18.8 Hz), 1.68-1.61 (1H, m), 1.49-1.42 (1H, m), 1.30 (3H, t, J=7.2 Hz), 1.04 (3H, s), 0.83 (3H, s).

Example 2

Optical purity of (S)-(+)-camphorsulfonic acid salt of ethyl (R)-3-amino-2,5-dioxopyrrolidine-3-carboxylate The optical purity of the crystal of the desired product (4.0 g, resolution yield: 88%) prepared by crystallizing the mixture of 3-amino-2,5-dioxopyrrolidine-3-carboxylate (4.0 g) and (S)-(+)-camphorsulfonic acid (5.0 g) from ethanol (20 ml) is 98% ee. This crystal was recrystallized from ethanol to give the crystal with optical purity of 99.9% ee (3.8 g, resolution yield 84%).

Reference Example 1

Preparation of ethyl 3-[N,N'-bis(benzyloxycarbonyl)hydrazino]-2,5-dioxopyrrolidine-3-carboxylate To a solution of ethyl 2,5-dioxopyrrolidine-3-carboxylate (3.92 g) in ethyl acetate (60 ml) was added dibenzyl azodicarboxylate (7.27 g), followed by potassium carbonate (317 mg) at room temperature. After this mixture was stirred at room temperature for 1 hour, the mixture was filtered through a Celite pad. The filtrate was concentrated and the resulting residue was purified by a flash column chromatography (hexane:ethyl acetate=2:1) to give the ethyl 3-[N,N'-bis(benzyloxycarbonyl)hydrazino]-2,5-dioxopyrrolidine-3-carboxylate (10.1 g, 94%) as amorphous.

$^1$H NMR (300 MHz, DMSO-d$_6$, 120° C.) δ: 11.4 (1H, br), 9.66 (1H, br), 7.35-7.25 (10H, m), 5.15-5.02 (4H, m), 4.14 (2H, q, J=7.1 Hz), 3.40 (1H, d, J=18.3 Hz), 3.17 (1H, d, J=18.2 Hz), 1.14 (3H, t, J=7.1 Hz).

Reference Example 2

Preparation of ethyl 3-hydrazino-2,5-dioxopyrrolidine-3-carboxylate

To a solution of the compound of Reference Example 1 (1.00 g) in ethanol (30 ml) was added 5% palladium-carbon ethylenediamine complex (100 mg). The mixture was stirred vigorously at room temperature under hydrogen (atmospheric pressure) for 2.5 hours. During this reaction, to remove the carbon dioxide generated with the progress of the reaction, the gas in the reactor was replaced with hydrogen gas several times. The reaction mixture was filtered through a Celite pad and then the Celite was washed with ethanol. The filtrate combined with the washers was concentrated to give the desired product (432 mg, quantitative) as oil $^1$H NMR (300 MHz, DMSO-d$_6$, 25° C.) δ: 4.16 (2H, q, J=7.1 Hz), 2.96 (1H, d, J=17.8 Hz), 2.86 (1H, d, J=17.9 Hz), 1.18 (3H, t, J=7.1 Hz).

Reference Example 3

Preparation of ethyl 3-hydrazino-2,5-dioxopyrrolidine-3-carboxylate monohydrochloride To a solution of ethyl 2,5-dioxopyrrolidine-3-carboxylate (2.96 g) in ethyl acetate (25 ml) were added di-tert-butyl azodicarboxylate (4.19 g) and then potassium carbonate (4.78 g) at room temperature. After this reaction mixture was stirred at room temperature for 15 minutes, the resulting mixture was filtered through a Celite pad and the filtrate was concentrated. The residue was purified by a flash column chromatography (hexane:ethyl acetate=3:1) to give ethyl 3-[N,N'-bis(tert-butyloxycarbonyl)hydrazino]-2,5-dioxopyrrolidine-3-carboxy late (5.77 g, 83%) as amorphous.

$^1$H NMR (300 MHz, DMSO-d$_6$, 120° C.) δ: 11.3 (1H, br), 8.80 (1H, br), 4.20 (2H, q, J=7.1 Hz), 3.41 (1H, d, J=18.1 Hz), 3.17 (1H, d, J=18.1 Hz), 1.41 (9H, s), 1.40 (9H, s), 1.23 (3H, t, J=7.1 Hz).

To a solution of ethyl 3-[N,N'-bis(tert-butyloxycarbonyl)hydrazino]-2,5-dioxopyrrolidine-3-carboxy late (5.77 g) in ethyl acetate (20 ml) was added a solution of 4M hydrogen chloride in ethyl acetate (25 ml) and the mixture was stirred at room temperature for 24 hours. The resulting precipitates were collected by filtering and washed with ethyl acetate to give the desired product (3.02 g, 76%) as powder. The desired product was identified to be a monohydrochloride salt thereof by the results of elementary analysis and X-ray crystallographic analysis.

Melting point: 189-190° C. (decomposition). $^1$H NMR (300 MHz, DMSO-d$_6$, 25° C.) δ: 12.1 (1H, br), 9.58 (3H, br), 4.23 (2H, q, J=7.0 Hz), 3.15 (2H, s), 1.22 (3H, t, J=7.1 Hz). Elementary analysis: Calculated for C$_7$H$_{12}$ClN$_3$O$_4$: C, 35.38; H, 5.09; Cl, 14.92; N, 17.68. Founded: C, 35.28; H, 5.02; Cl, 14.83; N, 17.68.

Reference Example 4

Preparation of ethyl 3-amino-2,5-dioxopyrrolidine-3-carboxylate

To a mixture of the compound of Reference Example 3 (274 mg), acetic acid (10 ml) and water (5 ml) was added platinum oxide (25.5 mg) and the mixture was stirred vigorously at 50° C. under hydrogen (atmospheric pressure) for 6 hours. The reaction mixture was filtered through a Celite pad and the Celite was washed with a small amount of acetic acid. To the mixture of the filtrate combined with the washers was added sodium acetate (164 mg) and the mixture was concentrated. To the residue was added toluene to remove azeotropically the residual acetic acid and water and then the mixture was concentrated again. To the residue was added ethyl acetate and the insoluble product was filtered off, and then the ethyl acetate solution was concentrated to give the crude product and it was purified by a flash column chromatography (chloroform:methanol=30:1) to give the desired product (122 mg, 66%) as crystal.

Example 3

Preparation of (S)-(+)-camphorsulfonic acid salt of ethyl (R)-3-amino-2,5-dioxopyrrolidine-3-carboxylate To a solution of the compound of Reference Example 1 (2.04 g) in acetic acid (30 ml) was added platinum oxide (393 mg) and the mixture was stirred vigorously at 50° C. under hydrogen (atmospheric pressure) for 8 hours. During this reaction, to remove carbon dioxide generated with the progress of the reaction, the gas in the reactor was replaced with hydrogen gas several times. The reaction mixture was filtered through a Celite pad and then the Celite was washed with a small amount of acetic acid. The filtrate combined with the washers was concentrated and to the resulting residue was added toluene to remove azeotropically the residual acetic acid and then the mixture was concentrated again. To the residue was added ethyl acetate and the insoluble product was filtered off and then the ethyl acetate solution was concentrated to give the crude product (918 mg). The crude product and (S)-(+)-camphorsulfonic acid (1.09 g) were dissolved in ethanol (40 ml) while warming and this solution was concentrated under reduced pressure to 4-5 ml in total. This resulting mixture was allowed to stand at room temperature and the precipitated crystal was collected by filtering and washed with ethanol to give the desired product (356 mg, 20%) as crystal.

Example 4

Preparation of ethyl (R)-2,5-dioxo-3-(pyrrol-1-yl)pyrrolidine-3-carboxylate (S)-(+)-Camphorsulfonic acid salt of ethyl (R)-3-amino-2,5-dioxopyrrolidine-3-carboxylate (418 mg) was dissolved in 25% aqueous acetic acid solution (4 ml). Thereto were added sodium acetate (82 mg) and 2,5-dimethoxytetrahydrofuran (0.143 ml) and the mixture was stirred at 70° C. for 1.5 hours. After allowed to cool, to this mixture was added ethyl acetate (20 ml) and then the mixture were washed with water, followed by saturated brine and dried over magnesium sulfate and filtered. The filtrate was concentrated to give an oil. This was purified by a flash column chromatography (hexane:ethyl acetate=3:1) to give the desired product (230 mg, 97%) as oil. $^1$H NMR data of this product were consistent with those described in J. Med. Chem., 1998, 41, p. 4118 to 4129.

$^1$H NMR (400 MHz, CDCl$_3$, 23° C.) δ: 9.05 (1H, br), 6.94 (2H, t, J=2.2 Hz), 6.26 (2H, t, J=2.2 Hz), 4.28 (2H, q, J=7.2 Hz), 3.59 (1H, d, J=17.6 Hz), 3.36 (1H, d, J=18.0 Hz), 1.26 (3H, t, J=7.2 Hz). $^{13}$C NMR (100 MHz, CDCl$_3$, 24° C.) δ: 172.7, 170.5, 166.8, 120.0, 110.1, 68.6, 63.9, 41.9, 13.8. MS (APCI): 237(M+H).

Example 5

Preparation of ethyl (R)-2,5-dioxo-3-(pyrrol-1-yl)pyrrolidine-3-carboxylate by an alternative method (S)-(+)-Camphorsulfonic acid salt of ethyl (R)-3-amino-2,5-dioxopyrrolidine-3-carboxylate (2.25 g) was dissolved in 25% aqueous acetic acid (8 ml). Thereto were added NaHCO$_3$ (0.5 g) and then 2,5-dimethoxytetrahydrofuran (0.74 g) and the mixture was stirred at 70° C. for 1.5 hours. After allowed to cooling, to this mixture were added water and ethyl acetate, and the ethyl acetate layer was separated. The ethyl acetate layer was washed with 30% brine twice, dried over magnesium sulfate and filtered. The filtrate was concentrated to give the desire product (1.2 g, 94%) as oil.

Example 6

Preparation of ethyl (R)-2,5-dioxo-3-(pyrrol-1-yl)pyrrolidine-3-carboxylate by an alternative method A mixture of (S)-(+)-camphorsulfonic acid salt of ethyl (R)-3-amino-2,5-dioxopyrrolidine-3-carboxylate (1.0 g), 2,5-dimethoxytetrahydrofuran (0.32 g), water (5 ml) and ethyl acetate (8 ml) was stirred at room temperature overnight. The mixture was extracted with ethyl acetate and the ethyl acetate layer was washed sequentially with water, 5% aqueous NaHCO$_3$ solution and then brine, dried over magnesium sulfate and filtered. The filtrate was concentrated to give the desired product (about 83% yields) containing about 5% impurity.

Example 7

Preparation of (3R)-2'-(4-bromo-2-fluorobenzyl)spiro[pyrrolidine-3,4'(1'H)-pyrrolo[1,2-a]pyr azine]-1',2,3',5(2H')-tetraone (1) To a solution of ethyl (R)-2,5-dioxo-3-(pyrrol-1-yl)pyrrolidine-3-carboxylate (767 mg) in ethyl acetate (10 ml) was added trichloroacetyl chloride (1.1 ml) and this solution was heated under reflux overnight. This reaction mixture was allowed to cool to room temperature, and thereto was added trichloroacetyl chloride (1.1 ml) and this mixture was heated under reflux for 3 hours. This reaction mixture was allowed to water-cooling to room temperature and the residual trichloroacetyl chloride was decomposed carefully with saturated aqueous sodium bicarbonate solution. After the aqueous layer was confirmed to be alkali, this mixture was extracted with ethyl acetate (5 ml) three times and the combined extract was washed sequentially with water and saturated brine, dried over magnesium sulfate, filtered and then concentrated to give a crude product as oil. This was purified by a flash column chromatography (n-hexane:ethyl acetate=1:1) to give ethyl (R)-2,5-dioxo-3-(2-trichloroacetylpyrrol-1-yl)pyrrolidine-3-carboxylate (1.17 g, 94%).

$^1$H NMR (400 MHz, DMSO-d$_6$, 22° C.) δ: 12.4 (br s, 1H), 7.68 (dd, 1H, J=1.2, 4.4 Hz), 7.55 (dd, 1H, J=1.6, 2.8 Hz), 6.44 (dd, 1H, J=2.4, 4.4 Hz), 4.25-4.08 (m, 2H), 3.72 (d, 1H, J=18.0 Hz), 3.06 (d, 1H, J=18.0 Hz), 1.11 (t, 3H, 7.2 Hz).
(2) To a solution of 4-bromo-2-fluorobenzylamine (0.93 g) and triethylamine (1.3 ml) in N,N-dimethylformamide (5 ml) was added a solution of ethyl (R)-2,5-dioxo-3-(2-trichloroacetylpyrrol-1-yl)pyrrolidine-3-carboxylate (1.16 g) in N,N-dimethylformamide (3 ml) dropwise at room temperature. This mixture was stirred at room temperature for 8 hours. This reaction mixture was diluted with ethyl acetate, then washed sequentially with 1 M hydrochloric acid (three times), water (four times) and saturated brine, dried over magnesium sulfate, filtered and concentrated to give a crude product as yellow oil. This was purified by flash column chromatography (n-hexane:ethyl acetate=2:1) to give (3R)-2'-(4-bromo-2-fluorobenzyl)spiro[pyrrolidine-3,4'(1'H)-pyrrolo[1,2-a]pyrazine]-1',2,3',5(2H')-tetraone (831 mg, 65%). This product was further crystallized from n-hexane-ethyl acetate to give the desired product (385 mg) as crystal.

Mp: 189-191° C. $^1$H NMR (400 MHz, DMSO-$d_6$, 22° C.) δ: 12.2 (br s, 1H), 7.73 (dd, 1H, J=2.0, 3.2 Hz), 7.55 (dd, 1H, J=2.0, 9.6 Hz), 7.36 (dd, 1H, J=2.0, 8.4 Hz), 7.17-7.12 (m, 2H), 6.53 (dd, 1H, J=2.8, 4.0 Hz), 5.04 (d, 1H, J=15.2 Hz), 4.96 (d, 1H, J=15.6 Hz), 3.57 (s, 2H).

Comparative Example 1.1

Optical resolution of ethyl 3-amino-2,5-dioxopyrrolidine-3-carboxylate with L-(+)-tartaric acid The inventors confirmed that a salt of ethyl (R)-3-amino-2,5-dioxopyrrolidine-3-carboxylate with L-(+)-tartaric acid and a salt of ethyl (S)-3-amino-2,5-dioxopyrrolidine-3-carboxylate with L-(+)-tartaric acid were both crystallized in acetonitrile. That is, it was confirmed that it is probably difficult to achieve the optical resolution of ethyl 3-amino-2,5-dioxopyrrolidine-3-carboxylate with L-(+)-tartaric acid using acetonitrile as solvent.

Comparative Example 1.2

Optical resolution of ethyl 3-amino-2,5-dioxopyrrolidine-3-carboxylate with S-(+)-mandelic acid A salt of 3-amino-2,5-dioxopyrrolidine-3-carboxylate (3.0 g) with S-(+)-mandelic acid (2.5 g) was crystallized in acetonitrile (4 ml) to give the desired salt (2.0 g, resolution yield 75%, optical purity 92% ee). It was difficult to further purify by recrystallization since this resulting salt was highly-soluble in acetonitrile. Additionally, the inventors did not find an effective crystallization solvent instead of acetonitrile.

Comparative Example 1.3

Optical resolution of ethyl 3-amino-2,5-dioxopyrrolidine-3-carboxylate with (−)-O,O'-dibenzoyl-L-tartaric acid A salt of 3-amino-2,5-dioxopyrrolidine-3-carboxylate (3.0 g) with (−)-O,O'-dibenzoyl-L-tartaric acid (6.1 g) was crystallized in acetonitrile (11 mL) to give the desire salt (3.2 g, resolution yield 69%, optical purity 97% ee). It was difficult to further purify by recrystallization since this resulting salt was highly-soluble in acetonitrile. Additionally, the inventors did not find an effective crystallization solvent instead of acetonitrile.

Comparative Example 1.4

Optical resolution of ethyl 3-amino-2,5-dioxopyrrolidine-3-carboxylate with other optically active acids The inventors tried to perform an optical resolution of ethyl 3-amino-2,5-dioxopyrrolidine-3-carboxylate with (+)-camphor acid, L-pyroglutamilic acid [(S)-(−)-2-pyrrolidone-5-carboxylic acid] or L-malic acid using acetonitrile as solvent, but could not obtain any salts.

Comparative Example 2

Preparation of ethyl (R)-3-amino-2,5-dioxopyrrolidine-3-carboxylate from (S)-(+)-camphorsulfonic acid salt of ethyl (R)-3-amino-2,5-dioxopyrrolidine-3-carboxylate To an aqueous 5% NaHCO$_3$ solution (10 ml) was added (S)-(+)-camphorsulfonic acid salt of ethyl (R)-3-amino-2,5-dioxopyrrolidine-3-carboxylate (2.09 g). During this addition, the reaction mixture was formed heavily. Then thereto was added NaCl and the mixture was extracted with ethyl acetate (30 ml) three times. First extraction gave the desire product (0.5 g, 54%). Further extractions with ethyl acetate (30 ml) twice gave the desire product in 0.2 g (second extraction) and 0.07 g (third extraction). Total amounts: 0.77 g (83%).

Ethyl (R)-3-amino-2,5-dioxopyrrolidine-3-carboxylate was very highly-soluble in water, and thus the extraction efficiency of it from the aqueous solution with organic solvent was low.

INDUSTRIAL APPLICABILITY

The compound represented by the formula (III) of the present invention is useful as an intermediate of Ranirestat being useful as a therapeutic agent for diabetic complications, and thus Ranirestat can be prepared efficiently using this compound.

The invention claimed is:

1. A process for preparing (3R)-2'-(4-bromo-2-fluorobenzyl)spiro-[pyrrolidine-3,4'(1'H)-pyrrolo[1,2-a]pyrazine]-1',2,3',5(2H')-tetraone, comprising the following steps:

(1) reacting a compound of the formula (III)

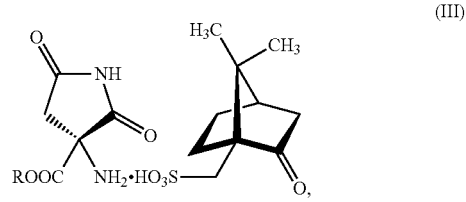

wherein R is a C$_{1-6}$ alkyl group,
with 2,5-dimethoxytetrahydrofuran to provide a compound of the formula (IV)

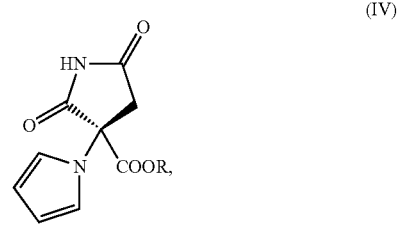

wherein R is a C$_{1-6}$ alkyl group;

(2) reacting the compound of the formula (IV)

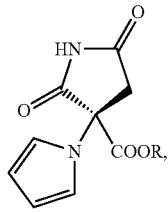
(IV)

wherein R is a $C_{1-6}$ alkyl group,
with trichloroacetyl chloride to provide a compound of the formula

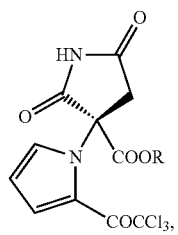

wherein R is a $C_{1-6}$ alkyl group; and
(3) reacting the compound provided in step (2) with 4-bromo-2-fluorobenzylamine to provide (3R)-2'-(4-bromo-2-fluorobenzyl)spiro-[pyrrolidine-3,4'(1'H)-pyrrolo[1,2-a]pyrazine]-1',2,3',5(2H')-tetraone.

2. A process for preparing (3R)-2'-(4-bromo-2-fluorobenzyl)spiro-[pyrrolidine-3,4'(1'H)-pyrrolo[1,2-a]pyrazine]-1',2,3',5(2H')-tetraone, comprising the following steps:
(1) reacting a compound of the formula (III)

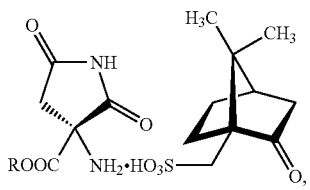
(III)

wherein R is a $C_{1-6}$ alkyl group,
with 2,5-dimethoxytetrahydrofuran in the presence of a base to provide a compound of the formula (IV)

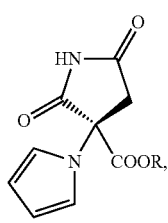
(IV)

wherein R is a $C_{1-6}$ alkyl group;

(2) reacting the compound of the formula (IV)

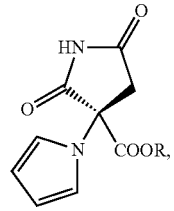
(IV)

wherein R is a $C_{1-6}$ alkyl group,
with trichloroacetyl chloride to provide a compound of the formula

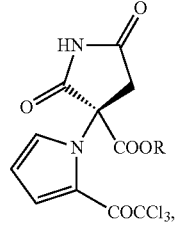

wherein R is a $C_{1-6}$ alkyl group; and
(3) reacting the compound provided in step (2) with 4-bromo-2-fluorobenzylamine to provide (3R)-2'-(4-bromo-2-fluorobenzyl)spiro-[pyrrolidine-3,4'(1'H)-pyrrolo[1,2-a]pyrazine]-1',2,3',5(2H')-tetraone.

3. A process for preparing (3R)-2'-(4-bromo-2-fluorobenzyl)spiro-[pyrrolidine-3,4'(1'H)-pyrrolo[1,2-a]pyrazine]-1', 2,3',5(2H')-tetraone, comprising the following steps:
(1) reacting a compound of the formula (III)

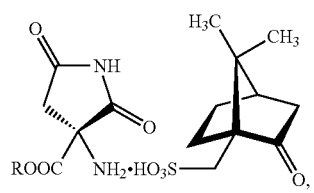
(III)

wherein R is a $C_{1-6}$ alkyl group,
with 2,5-dimethoxytetrahydrofuran in the presence of sodium acetate to provide a compound of the formula (IV)

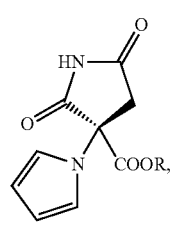
(IV)

wherein R is a $C_{1-6}$ alkyl group;

(2) reacting the compound of the formula (IV)

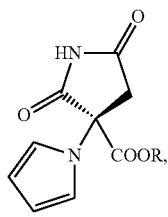

(IV)

wherein R is a $C_{1-6}$ alkyl group,
with trichloroacetyl chloride to provide a compound of the formula

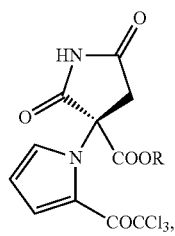

wherein R is a $C_{1-6}$ alkyl group; and
(3) reacting the compound provided in step (2) with 4-bromo-2-fluorobenzylamine to provide (3R)-2'-(4-bromo-2-fluorobenzyl)spiro-[pyrrolidine-3,4'(1'H)-pyrrolo[1,2-a]pyrazine]-1',2,3',5(2H')-tetraone.

4. A process for preparing (3R)-2'-(4-bromo-2-fluorobenzyl)spiro-[pyrrolidine-3,4'(1'H)-pyrrolo[1,2-a]pyrazine]-1',2,3',5(2H')-tetraone, comprising the following steps:
(1) reacting a compound of the formula (III)

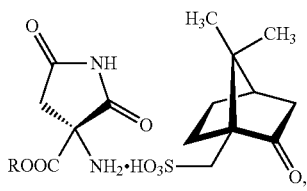

(III)

wherein R is ethyl,
with 2,5-dimethoxytetrahydrofuran to provide a compound of the formula (IV)

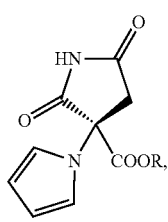

(IV)

wherein R is ethyl;

(2) reacting the compound of the formula (IV)

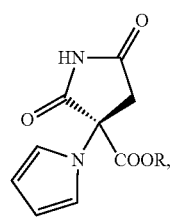

(IV)

wherein R is ethyl,
with trichloroacetyl chloride to provide a compound of the formula

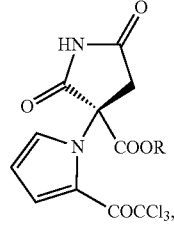

wherein R is ethyl; and
(3) reacting the compound provided in step (2) with 4-bromo-2-fluorobenzylamine to provide (3R)-2'-(4-bromo-2-fluorobenzyl)spiro[pyrrolidine-3,4'(1'H)-pyrrolo[1,2-a]pyrazine]-1',2,3',5(2H')-tetraone.

5. A process for preparing (3R)-2'-(4-bromo-2-fluorobenzyl)spiro-[pyrrolidine-3,4'(1'H)-pyrrolo[1,2-a]pyrazine]-1', 2,3',5(2H')-tetraone, comprising the following steps:
(1) reacting a compound of the formula (III)

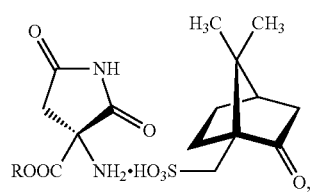

(III)

wherein R is a $C_{1-6}$ alkyl group,
with 2,5-dimethoxytetrahydrofuran in the presence of a base in acetic acid to provide a compound of the formula (IV)

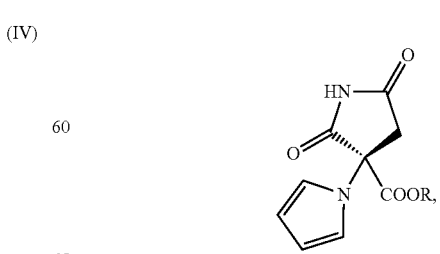

(IV)

wherein R is a $C_{1-6}$ alkyl group;

(2) reacting the compound of the formula (IV)

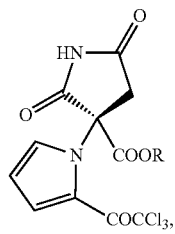

wherein R is a $C_{1-6}$ alkyl group,
with trichloroacetyl chloride to provide a compound of the formula

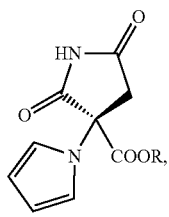

wherein R is a $C_{1-6}$ alkyl group; and
(3) reacting the compound provided in step (2) with 4-bromo-2-fluorobenzylamine to provide (3R)-2'-(4-bromo-2-fluorobenzyl)spiro[pyrrolidine-3,4'(1'H)-pyrrolo[1,2-a]pyrazine]-1',2,3',5(2H')-tetraone.

6. A process for preparing (3R)-2'-(4-bromo-2-fluorobenzyl)spiro-[pyrrolidine-3,4'(1'H)-pyrrolo[1,2-a]pyrazine]-1',2,3',5(2H')-tetraone, comprising the following steps:
(1) reacting a compound of the formula (III)

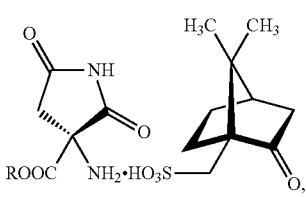

wherein R is a $C_{1-6}$ alkyl group,
with 2,5-dimethoxytetrahydrofuran in the presence of sodium acetate in acetic acid to provide a compound of the formula (IV)

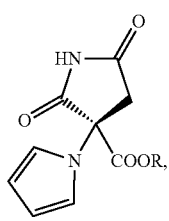

wherein R is a $C_{1-6}$ alkyl group;

(2) reacting the compound of the formula (IV)

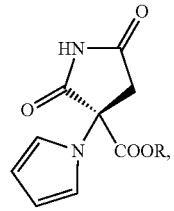

wherein R is a $C_{1-6}$ alkyl group,
with trichloroacetyl chloride to provide a compound of the formula

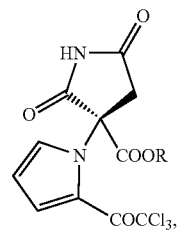

wherein R is a $C_{1-6}$ alkyl group; and
(3) reacting the compound provided in step (2) with 4-bromo-2-fluorobenzylamine to provide (3R)-2'-(4-bromo-2-fluorobenzyl)spiro[pyrrolidine-3,4'(1'H)-pyrrolo[1,2-a]pyrazine]-1',2,3',5(2H')-tetraone.

7. A process for preparing (3R)-2'-(4-bromo-2-fluorobenzyl)-spiro-[pyrrolidine-3,4'(1'H)-pyrrolo[1,2-a]pyrazine]-1',2,3',5(2H')-tetraone, comprising the following steps:
(1) admixing a compound of the formula (II):

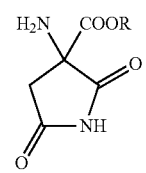

wherein R is a $C_{1-6}$ alkyl group,
with (S)-camphorsulfonic acid dissolved in an alcohol to provide the following mixture:

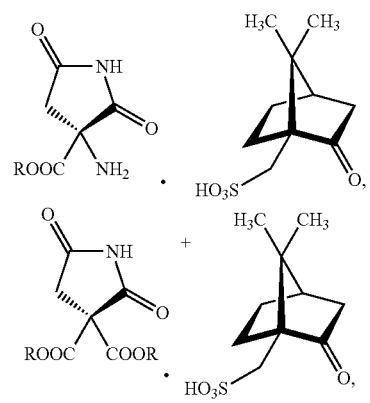

wherein each R is independently a $C_{1-6}$ alkyl group;

(2) crystallizing a compound of the formula (III)

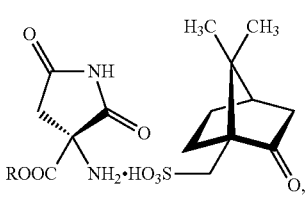

wherein R is a $C_{1-6}$ alkyl group,
from the mixture provided in step (1);
(3) reacting the crystalline compound of the formula (III) with 2,5-dimethoxytetrahydrofuran to provide a compound of the formula (IV)

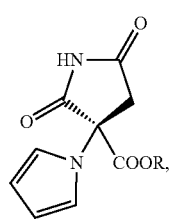

wherein R is a $C_{1-6}$ alkyl group;
(4) reacting a compound of the formula (IV)

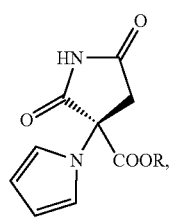

wherein R is a $C_{1-6}$ alkyl group,
with trichloroacetyl chloride to provide a compound of the formula

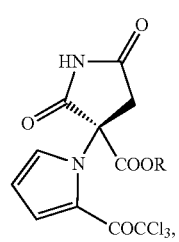

wherein R is a $C_{1-6}$ alkyl group; and
(5) reacting the compound provided in step (4) with 4-bromo-2-fluorobenzylamine to provide (3R)-2'-(4-bromo-2-fluorobenzyl)spiro-[pyrrolidine-3,4'(1'H)-pyrrolo[1,2-a]pyrazine]-1',2,3',5(2H')-tetraone.

8. A process for preparing (3R)-2'-(4-bromo-2-fluorobenzyl)spiro-[pyrrolidine-3,4'(1'H)-pyrrolo[1,2-a]pyrazine]-1',2,3',5(2H')-tetraone, comprising the following steps:

(1) hydrogenating a compound of the formula (I):

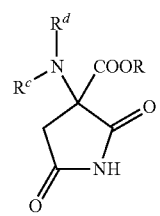

wherein R is a $C_{1-6}$ alkyl group, and
when $R^c$ is a hydrogen atom, then $R^d$ is a benzyloxycarbonyl group or an amino group, or
when $R^c$ is a benzyloxycarbonyl group, then $R^d$ is a benzyloxycarbonylamino group,
to provide a compound of the formula (II):

(II)

[structure]

wherein R is a $C_{1-6}$ alkyl group;
(2) reacting the compound of the formula (II)

(II)

[structure]

with (S)-camphorsulfonic acid, in situ, to provide the following mixture:

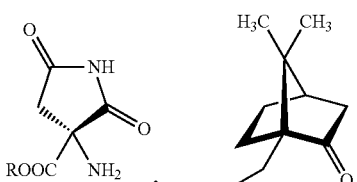

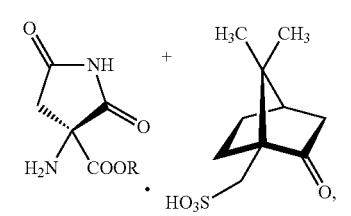

wherein each R is independently a $C_{1-6}$ alkyl group;

(3) crystallizing a compound of the formula (III),

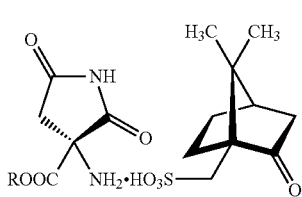

(III)

wherein R is a C$_{1-6}$ alkyl group,
from the mixture provided in step (2);
(4) isolating the crystalline compound of the formula (III)

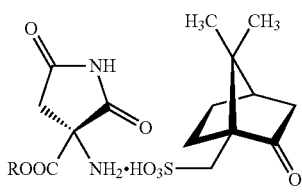

(III)

wherein R is a C$_{1-6}$ alkyl group;
(5) reacting the crystalline compound of the formula (III) with 2,5-dimethoxytetrahydrofuran to provide a compound of the formula (IV)

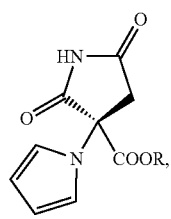

(IV)

wherein R is a C$_{1-6}$ alkyl group;

(6) reacting the compound of the formula (IV)

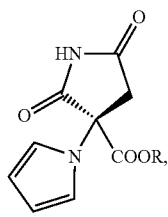

(IV)

wherein R is a C$_{1-6}$ alkyl group,
with trichloroacetyl chloride to provide a compound of the formula

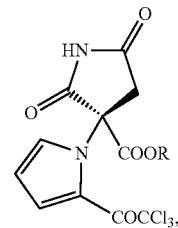

wherein R is a C$_{1-6}$ alkyl group; and
(7) reacting the compound provided in step (6) with 4-bromo-2-fluorobenzylamine to provide (3R)-2'-(4-bromo-2-fluorobenzyl)spiro-[pyrrolidine-3,4'(1'H)-pyrrolo[1,2-a]pyrazine]-1',2,3',5(2H')-tetraone.

* * * * *